US009121696B2

(12) United States Patent
Jin et al.

(10) Patent No.: US 9,121,696 B2
(45) Date of Patent: Sep. 1, 2015

(54) DEVICE AND METHOD FOR MEASURING VIA HOLE OF SILICON WAFER

(75) Inventors: Jong Han Jin, Daejeon (KR); Jae Wan Kim, Daejeon (KR); Jong Ahn Kim, Daejeon (KR); Chu-Shik Kang, Daejeon (KR)

(73) Assignee: KOREA RESEARCH INSTITUTE OF STANDARDS AND SCIENCE (KR)

( * ) Notice: Subject to any disclaimer, the term of this patent is extended or adjusted under 35 U.S.C. 154(b) by 155 days.

(21) Appl. No.: 13/820,575

(22) PCT Filed: Jun. 24, 2011

(86) PCT No.: PCT/KR2011/004616
§ 371 (c)(1),
(2), (4) Date: Mar. 4, 2013

(87) PCT Pub. No.: WO2011/162566
PCT Pub. Date: Dec. 29, 2011

(65) Prior Publication Data
US 2013/0206992 A1 Aug. 15, 2013

(30) Foreign Application Priority Data
Jun. 24, 2010 (KR) .................. 10-2010-0059994

(51) Int. Cl.
*G01J 5/02* (2006.01)
*G01B 11/22* (2006.01)
(Continued)

(52) U.S. Cl.
CPC ............ *G01B 11/22* (2013.01); *G01B 9/02008* (2013.01); *G01B 11/12* (2013.01); *G01N 21/9501* (2013.01); *G01B 2210/56* (2013.01); *G01N 2021/95653* (2013.01)

(58) Field of Classification Search
CPC .................................................. G01N 21/3563
USPC .................................................... 250/339.11
See application file for complete search history.

(56) References Cited

U.S. PATENT DOCUMENTS

2005/0111008 A1 5/2005 Murata
2008/0073752 A1 3/2008 Asai et al.
(Continued)

FOREIGN PATENT DOCUMENTS

JP 11274259 10/1999
JP 2002228420 8/2002
(Continued)

OTHER PUBLICATIONS

International Search Report—PCT/KR2011/004616 dated Mar. 9, 2012.
(Continued)

*Primary Examiner* — David Porta
*Assistant Examiner* — Hugh H Maupin
(74) *Attorney, Agent, or Firm* — Cantor Colburn LLP

(57) ABSTRACT

The present invention pertains to a device and a method for measuring a via hole of a silicon wafer, wherein it is possible to precisely measure the depth of the via hole without damaging the wafer. Broadband infrared light is radiated to a silicon wafer which has a superior light transmission property, so that the depth of the via hole may be measured from the light which is reflected from each boundary surface of the wafer and the interference signal of reference light. The via hole measuring device according to the present invention includes: a light source unit for generating broadband infrared light; and an interferometer for radiating the light generated from the light source unit to a silicon wafer, so as to measure the depth of a via hole formed on the wafer according to the spectrum period of the interference signal of the light, which is reflected from the silicon wafer.

10 Claims, 4 Drawing Sheets

(51) Int. Cl.
*G01B 11/12* (2006.01)
*G01B 9/02* (2006.01)
*G01N 21/95* (2006.01)
*G01N 21/956* (2006.01)

(56) References Cited

U.S. PATENT DOCUMENTS

2009/0296758 A1* 12/2009 Brown et al. .................. 372/25
2010/0321671 A1* 12/2010 Marx et al. .................... 356/51

FOREIGN PATENT DOCUMENTS

| | | |
|---|---|---|
| JP | 2008085020 | 4/2008 |
| JP | 2009036563 | 2/2009 |
| KR | 1020050032491 | 4/2005 |

OTHER PUBLICATIONS

Korean Office Action—Korean Application No. 10-2012-7012430 issued on Aug. 24, 2012, citing JP2002-228420 and JP2009-036563.

* cited by examiner

DEVICE AND METHOD FOR MEASURING VIA HOLE OF SILICON WAFER

TECHNICAL FIELD

The present invention relates to a device and a method for measuring a via hole, and more specifically, to a device and a method for measuring a via hole of a silicon wafer, which are capable of accurately measuring a depth and a diameter of a via hole without damaging the wafer.

BACKGROUND ART

A fine line width has been implemented through exposure in order to implement a highly integrated semiconductor circuit, but the line width that can be implemented is limited due to a diffraction limit.

In order to overcome this, a method of reducing a diffraction limit using a light having a shorter wavelength than a visible light, such as extreme ultraviolet (EUV), and a 3D semiconductor packaging process of vertically stacking a number of wafer chips subjected to a process to increase an degree of integration have been proposed.

In the 3D semiconductor packing process in which a number of wafer chips are vertically stacked, circuits of respective wafer layers should be electrically connected to constitute circuits that send and receive electrical signals between a number of stacked wafer chips. For electrical connection between the wafer layers, elongate holes (hereinafter referred to as "via holes") called through silicon vias (TSVs) are formed in the silicon wafer and the via holes are filled with a conductive material to connect the circuits between the wafer layers. Currently, a TSV process can be implemented, for example, through deep etching.

Such a via hole has a structure in which a diameter is small and a depth is large as described above, i.e., an aspect ratio is great. Accordingly, it is difficult to confirm whether a formed via hole is successfully formed to have a desired predetermined depth and diameter.

Via holes should be formed to have the same depth and diameter on one wafer. If the wafer chip is stacked on another wafer chip after grinding when the via holes are formed with different diameters or depths, some circuits may not be electrically connected and a product defect may be caused. Accordingly, inspecting whether the via holes formed in the wafer are formed with a predetermined depth and diameter is an important process in a process of fabricating a 3D semiconductor package.

As a conventional method of inspecting a depth and a diameter of the via hole of the silicon wafer, there are an optical measurement method of irradiating a light to a wafer surface in which via holes are formed to measure the depth and the diameter, a method of cutting a cross-section of a wafer in which via holes are formed and performing inspection using a scanning electron microscope (SEM), and the like. In the conventional optical measurement method, in the case of a measurement method using a confocal microscope, it is difficult to make accurate depth decision due to a great depth measurement error caused by diffuse reflection at a side surface of the via hole and a bottom surface, and in the case of a measurement method using a white-light scanning interferometer, it is difficult to accurately measure the depth of the via hole due to a light not reaching the bottom surface of the via hole by a high aspect ratio of a measurement specimen or due to a diffraction phenomenon occurring at a via hole entrance.

The method using a scanning electron microscope (SEM) has a drawback in that it damages a specimen, and accordingly cannot be used for total wafer inspection in a semiconductor packaging process.

SUMMARY OF INVENTION

Technical Problems

The present invention has been made to resolve the problems of the related art as described above, and an object of the present invention is to provide a device and a method for measuring a via hole of a silicon wafer, which capable of accurately measuring a depth and a diameter of a via hole formed in a silicon wafer without damaging the wafer silicon.

Another object of the present invention is to provide a device and a method capable of measuring a depth of a via hole of a silicon wafer rapidly and with high resolution.

Another object of the present invention is to provide a device and a method for measuring a depth and a diameter of a via hole of a silicon wafer, which can reduce a measurement noise due to external vibration.

Another object of the present invention is to provide a device and a method for measuring a via hole of a silicon wafer, which are capable of measuring a depth and a diameter of the via hole with high precision even when the diameter of the via hole is small, by irradiating a surface opposite to a surface having the via hole formed therein with a light in an infrared band, sensing an interference signal of a light reflected by a bottom surface of the via hole, and measuring a depth and a diameter of the via hole formed in the wafer.

Solution to Problem

In order to achieve the above object, a device for measuring a via hole of a silicon wafer according to the present invention includes a light source unit, and an interferometer that irradiates a light generated from the light source unit to the silicon wafer and measures a depth of the via hole formed in the wafer from an interference signal of a light reflected by the silicon wafer. The light source unit generates a broadband infrared light, the interferometer senses an interference signal that is generated as the broadband infrared light is reflected by interfaces of a bottom surface of the via hole and a front surface or a rear surface of the silicon wafer, and optical path differences for a plurality of frequency components are simultaneously acquired through spectrum period analysis for the interference signal to measure a depth and a diameter of the via hole.

The interferometer preferably includes a collimation lens that converts the light output from the light source unit to a parallel light; a beam splitter that transmits a light passing through the collimation lens and reflects the light reflected by the wafer to split a path of the light; and a detector that uses a light reflected by one of the surfaces of the wafer among the lights reflected by the wafer as a reference light and detects an interference signal that is a combination of a measurement light and the reference light.

The interferometer may include a spectrum analyzer and acquire an interference signal according to each frequency component. The detector preferably includes an optical spectrum analyzer.

According to another embodiment of the present invention, the interferometer includes: a collimation lens that converts the light output from the light source unit to a parallel light; a beam splitter that transmits a light passing through the collimation lens and reflects the lights reflected by the wafer to split a path of the light; a detector that detects an interference signal that is a combination of a measurement light reflected by the surface of the wafer among the lights reflected by the wafer and a reference light; and a reference mirror that provides the reference light to the detector using the light reflected by the beam splitter.

According to a preferred embodiment of the present invention, the interferometer is provided to face a surface opposite to the surface of the silicon wafer in which the via hole has been formed, and senses a light obtained as a broadband infrared irradiated from the light source is transmitted through the silicon wafer and reflected by an interface of the bottom surface of the via hole or the opposite surface of the wafer.

The light source unit preferably includes: a seed laser that generates a single wavelength laser light in an infrared region; a frequency generator that generates a broadband infrared light from the infrared laser light output by the seed laser; and an amplifier that amplifies the broadband infrared light generated by the frequency generator to have a light amount sufficient to be applied to the interferometer.

The broadband infrared light generated by the light source unit may have a frequency interval ranging from 1 kHz to 100 GHz and a bandwidth ranging from 0.1 nm to 2000 nm.

The broadband infrared light generated by the light source unit preferably is a pulse laser whose repetition rate ranging from 1 kHz to 100 GHz and bandwidth ranging from 0.1 nm to 2000 nm.

According to a preferred embodiment of the present invention, the interferometer includes: a collimation lens that converts the broadband infrared light output from the light source unit to a parallel light; a condenser lens that is arranged to face the collimation lens with the silicon wafer interposed therebetween, and condenses the infrared light transmitted through the silicon wafer after passing through the collimation lens; a detector that is arranged to face the condenser lens and detects an interference signal caused by an optical path difference between an infrared light passing through the via hole formed in the silicon wafer and an infrared light transmitted through a portion of the silicon wafer in which a via hole has not been formed.

In a via hole measurement method using a device for measuring a via hole of a silicon wafer according to an embodiment of the present invention, preferably, the broadband infrared light from the light source unit is irradiated to the front surface or the rear surface of the silicon wafer and reflected by interfaces of both surfaces of the silicon wafer and the bottom surface of the via hole, a light reflected by one of the surfaces of the wafer is used as the reference light, and an interference signal of the reference light and the infrared light reflected by the bottom surface of the via hole is measured to measure the depth of the via hole.

In a via hole measurement method using a device for measuring a via hole of a silicon wafer according to an embodiment of the present invention, the broadband infrared light from the light source unit is irradiated to the silicon wafer and reflected by interfaces of both surfaces of the silicon wafer and the interface of the bottom surface of the via hole, and an interference signal of the reflected light and the reference light reflected by the reference mirror is measured to measure the depth of the via hole.

The interference signal of the lights reflected by the interfaces of both surfaces of the silicon wafer and the interface of the bottom surface of the via hole and the reference light may be measured to measure the diameter of the via hole while finely moving the wafer in a direction perpendicular to the broadband infrared light irradiated from the light source unit.

Advantageous Effects of Invention

According to the means of the present invention as described above, it is possible to accurately measure the depth and the diameter of the via hole formed in the silicon wafer without damaging the wafer silicon.

It is also possible to measure the depth and the diameter of the via hole of the silicon wafer rapidly and with high precision.

With the device and the method for measuring a via hole according to an embodiment of the present invention, via hole measurement resolution is improved and a signal to noise ratio is improved by using a pulse having a short pulse width.

With the device and the method for measuring a via hole according to a preferred embodiment of the present invention, it is possible to accurately confirm whether the via hole is defective rapidly in a non-destructive manner. Accordingly, utilization in the 3D semiconductor packing process is excellent, the yield of a semiconductor package is improved, and influence of mechanical vibration on measurement quality is minimized.

DESCRIPTION OF EMBODIMENTS

Hereinafter, a device for measuring a via hole of a silicon wafer according to the present invention will be described in detail with reference to the accompanying drawings.

A device for measuring a via hole of a silicon wafer according to an embodiment of the present invention is a device that measures a depth and a diameter of a via hole using an interference phenomenon of a light reflected by an interface of a bottom surface (hereinafter referred to as a bottom surface) of a via hole formed in a silicon wafer.

A semiconductor silicon wafer has a monocrystalline structure in which crystal is formed very uniformly. Accordingly, when light passes through a silicon wafer that is a single medium, the light is not refracted in the middle of the medium. Thus, it is possible to obtain information on a depth of the via hole from a light reflected by the interface of the bottom surface of the via hole and an outer interface of a front surface or a rear surface of the wafer.

Figure 1:
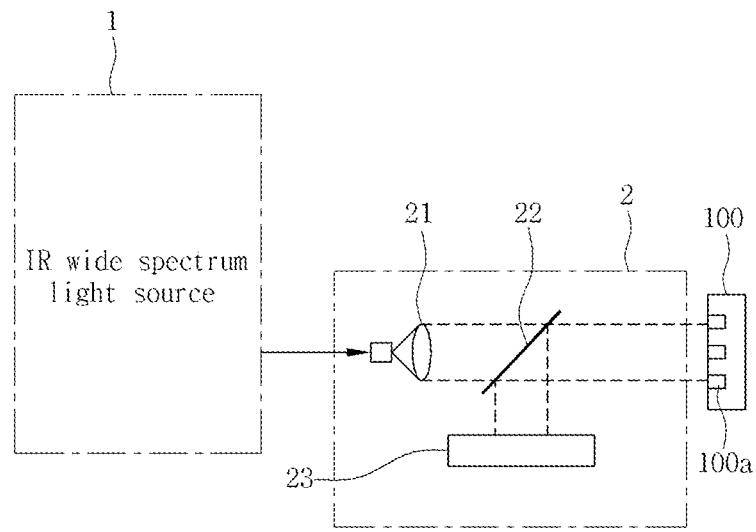
FIG. 1 is a diagram illustrating a configuration of a device for measuring a via hole of a silicon wafer according to an embodiment of the present invention.

The device for measuring a via hole of a silicon wafer according to an embodiment of the present invention includes a light source unit 1 and an interferometer 2, as illustrated in FIG. 1. The interferometer is a measuring instrument that splits a light emitted from the same light source to cause a travelling path difference and using an interference phenomenon observed from a combined light. The light source unit 1 generates a light to be irradiated to a silicon wafer, and the interferometer 2 measures a depth and a diameter of the via hole formed in the wafer from an interference signal of a light that is irradiated from the light source unit 1 to the silicon wafer and then reflected by the silicon wafer.

According to the present invention, the light source unit 1 generates a broadband infrared light. Since the infrared light has a transmission characteristic for the silicon wafer 100, the infrared light may be irradiated to either a front surface of the silicon wafer (an interface of a surface having the via hole formed therein; hereinafter referred to as a front surface) or a rear surface of the silicon wafer (an interface opposite to the surface having the via hole formed therein; hereinafter referred to as a rear surface). The depth of the via hole can be accurately measured by acquiring and processing an interference signal of a reflected infrared light reflected by the bottom surface of the via hole and a reference light without suffering from a problem of diffraction at the front surface of the via hole or a problem of the light not reaching the bottom surface of the via hole due to a high aspect ratio of the via hole, by irradiating the infrared light to the silicon wafer as described above.

The interferometer 2 is provided to face the front surface that is the surface of the silicon wafer in which the via hole has been formed or the rear surface that is an opposite surface, such that the light irradiated from the light source can be transmitted through the silicon wafer and reflected by the bottom surface of the via hole or the front surface or the rear surface of the wafer and a mutually interfered light can be sensed.

In general, an interference signal I(L) obtained from the interferometer is a function of an optical path difference L and is represented by the following equation:

$$I(L)=I_0(1+\gamma \cos(2\pi/c \cdot L \cdot f))$$

Here, $I_0$ is an intensity of a background light, $\gamma$ denotes visibility, c denotes a speed of the light, L denotes the optical path difference, and f denotes a frequency of the light source.

In general, when a single light is used, a reference mirror should be moved by a certain distance to obtain an accurate phase and acquire an interference pattern and the interference pattern should be analyzed to obtain distance information. However, in the present invention, since the infrared light having a broad bandwidth is used, an optical path difference L can be obtained by acquiring an interference signal according to the optical frequency f in a spectrum region and obtaining a period of the interference signal. Accordingly, using such a property of the light, the interferometer of the present invention can simultaneously obtain a number of optical path differences in real time by simultaneously acquiring broadband infrared interference signals and performing spectrum analysis without a scanning process of moving the reference mirror in an optical path direction, by applying the broadband infrared light to the silicon wafer. Accordingly, it is possible to rapidly measure the via hole depth and obtain excellent measurement precision.

It is desirable for the interferometer to include an optical spectrum analyzer and acquire an interference signal according to each frequency component.

In FIG. 1, the interferometer is provided in a position opposite to the front surface of the silicon wafer, the infrared light is directly incident on the via hole and reflected by the bottom surface of the via hole, a part of the infrared light is directly transmitted and reflected by the rear surface, and an interference signal of the two reflection components and a reference light is analyzed to calculate the depth of the via hole. A spectrum period of the interference signal can be obtained through Fourier transform. A method of filtering only a desired peak, performing inverse Fourier transform, and performing measurement based on a phase may be used to obtain a more accurate peak position in a Fourier region.

In a portion of the silicon wafer in which via holes have not been formed, the infrared light is reflected by two interfacial points of the front surface and the rear surface of the silicon wafer. Thickness information of the silicon wafer can be obtained from the reflected infrared light.

Hereinafter, a device and a method for measuring a via hole in which a broadband infrared light is irradiated to a rear surface of a silicon wafer to obtain an interference signal according to an embodiment of the present invention will be described in detail with reference to FIGS. 2 to 4. A device for measuring a via hole by irradiating an infrared light to a front surface of a silicon wafer and a device for measuring a via hole by irradiating an infrared light to a rear surface of a silicon wafer have the same structure except that the wafer is arranged in a different direction.

Figure 2:
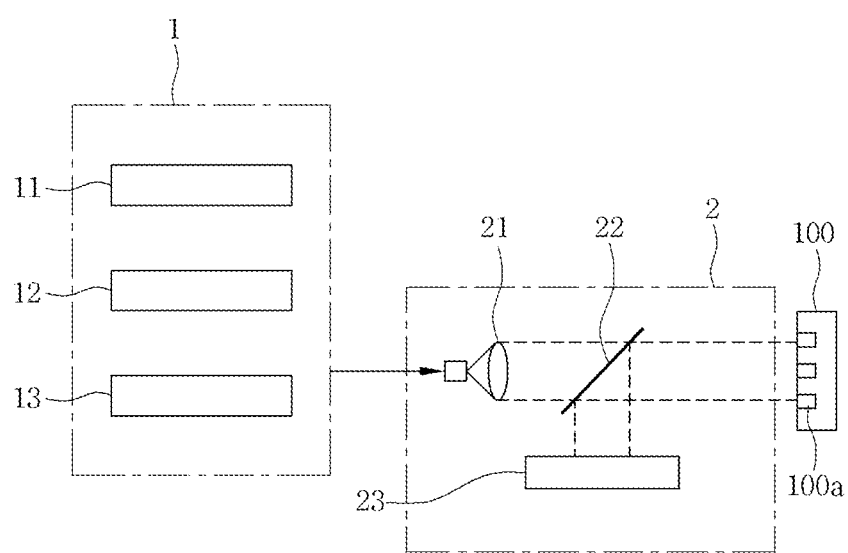
FIG. 2 is a diagram illustrating a configuration of a device for measuring a via hole of a silicon wafer according to an embodiment of the present invention, which is applied to a rear surface of the silicon wafer.

As illustrated in FIG. 2, a device for measuring a via hole of a silicon wafer according to the present invention is a via hole measurement device including a light source unit 1 that irradiates an infrared light having a wide bandwidth, and an interferometer 2 that measures a depth and a diameter of a via hole formed in a wafer from an interference signal of a light irradiated from the light source unit 1 and reflected by the silicon wafer. The interferometer 2 is provided to face a surface opposite to the surface of the silicon wafer in which the via hole has been formed to sense a light obtained as the irradiated light is transmitted through the wafer and reflected by the interface of the bottom surface of the via hole or the opposite surface of the wafer.

The light source unit 1 includes means that adjusts the light irradiated to the wafer 100 to be well transmitted through a material constituting the wafer. The light source unit 1 generates a broadband infrared light rather than a single frequency.

The light source unit 1 includes a seed laser having a single wavelength belonging to an infrared region, a frequency generator that generates a broadband light in an infrared region from the infrared light output from the seed laser, and an amplifier that amplifies the broadband infrared laser light generated by the frequency generator.

As illustrated in FIG. 2, the light source unit 1 according to an embodiment of the present invention includes a distributed feedback (DFB) laser 11 that generates a seed laser having a single wavelength whose center wavelength is 1541 nm, a frequency generator 12 that generates a broadband light from the laser light output from the DFB laser, and an amplifier 13 that amplifies the light generated by the frequency generator to have a light amount sufficient to be applied to the interferometer 2.

The broadband light generated by the frequency generator 12 is a broadband light having a spectrum whose repetition rate ranges from a few kHz to hundreds of GHz and bandwidth ranges from a few nm to hundreds of nm. Preferably, the repetition rate ranges from 1 kHz to 100 GHz, and the bandwidth ranges from 0.1 nm to 1000 nm.

The light irradiated by the configured light source unit 1 has a broad bandwidth such that an optical path difference can be obtained without phase shifting.

In the device for measuring a via hole of a silicon wafer according to the present invention, since the irradiated light can be transmitted through the silicon wafer 100 as described above, it is desirable to use light in an infrared band as the light to be irradiated to the silicon wafer 100.

The interferometer 2 is a device that splits a light irradiated from one light source in two or more to have an optical path difference and observes interference occurring when wave surfaces overlap. The interferometer 2 is widely used, for example, for a shape measuring device. As illustrated in FIG. 2, the interferometer 2 includes a collimation lens 21 that converts a light output from the light source unit 1 to a parallel light, a beam splitter 22 that transmits the light passing through the collimation lens 21 and reflects a light reflected by the wafer 100 to split a path of the light, and a detector 23 that uses a light reflected by the surface of the wafer among the lights reflected by the wafer 100 as a reference light and detects an interference signal that is a combination of a measurement light and the reference light. The detector includes an optical spectrum analyzer and detects an interference signal of the broadband infrared light.

In the configured interferometer 2, a reference light to be compared with the measurement light reflected by the wafer 100 is required. A light reflected by the interface of one of the surfaces among lights reflected by the interfaces of both surfaces of the wafer is defined as the reference light. It is possible to measure the depth of the via hole by measuring the interference signal of the reference light and the other measurement light.

By using the measurement light reflected by any one of the interfaces of the wafer 100 as the reference light, it is possible to reduce an error of the reference light that may be generated when a reference mirror, which will be described below, is provided. That is, even when the wafer 100 is vibrated, the reference light is a light reflected by the vibrated wafer. Thus, when the reference light is vibrated, the measurement light is also vibrated. Accordingly, when the reference light is set as the light reflected by any one of the interfaces of the wafer 100, it is possible to perfectly remove a vibration error the reference light and the measurement light.

Further, the measuring device of the present invention configured as described above is capable of measuring a diameter or a width of the via hole 100*a*. In a method of measuring the diameter or the width of the via hole 100*a*, the diameter of the via hole is measured by measuring an interference signal of the reflected measurement light and the reference light while finely moving the wafer 100 in a direction perpendicular to the light irradiated from the light source unit 1.

That is, it is possible to confirm the diameter or the width of the via hole 100*a* by confirming a region of the measurement light reflected by the interface of the bottom surface of the via hole 100*a*.

The interferometer 2 may further include a reference mirror 24 as means for generating the reference light.

The reference mirror 24 is means that generates the reference light using the light reflected by the beam splitter 22. The depth and the diameter or the width of the via hole 100*a* can be measured from an interference signal of the reference light and the measurement light.

When the reference mirror 24 is provided in this manner, an error of the reference light may be generated due to vibration of the reference mirror as described above. Accordingly, it is desirable to set the light reflected by any one of the interfaces of the wafer 100 as the reference light, as described above.

As described above, when the depth or the diameter is measured from the interference signal of the measurement light using the light reflected by any one of the interfaces of the wafer 100 as the reference light without using the reference mirror 24, it is possible to obtain a characteristic that the wafer 100 is insensitive to the vibration and realize real-time measurement in the process.

The device for measuring a via hole of a silicon wafer configured as described above according to the present invention and a measurement method using the device will be described in detail.

First, in the via hole measurement method, a light irradiated from the light source unit 1 is irradiated to the wafer 100, wherein the irradiated light is irradiated to a surface opposite to the via hole formed in the wafer 100*a*. The irradiated light is reflected by the interfaces of both surfaces of the wafer and the interface of the bottom surface of the hole 100*a*, and an interference signal of the reflected light and the reference light is used to measure the depth of the via hole.

The interferometer 2 is widely used for high-precision measurement since high measurement resolution as well as length standard traceability can be secured, but has a problem in that the reference mirror 24 should be moved or phase-inverted to determine a phase. Accordingly, the spectrum analysis is performed using a light source having a broad bandwidth, thereby obtaining the optical path difference without moving or phase-inverting the reference mirror 24.

FIG. 2 is a diagram illustrating a configuration of a measurement device according to the present invention as described above. The DFB laser 11 having a center wavelength of 1541 nm was used as the seed laser that is a light for use of a transmission characteristic of the silicon wafer 100. A light emitted from the DFB laser 11 is incident on the frequency generator 12 to generate a spectrum whose frequency ranges from 20 GHz to 30 GHz and bandwidth ranges from 15 nm to 25 nm.

A repetition rate of the frequency generator 12 is locked to a reference clock (Rb-reference clock) and stabilized, and an optical comb generated in this manner is amplified by the amplifier 13 to have a light amount sufficient to be actually applied to and used in the interferometer.

The amplified light is input to the interferometer 2, and the light collimated through the collimation lens 21 is split by the beam splitter 22 and incident on the wafer 100. A light reflected by the interface of any one of the surfaces among lights reflected and returned from silicon wafer 100 is used as the reference light. An interference signal of the reference light and the measurement light is detected by the detector 23 and calculated to measure the depth and the diameter or the width of the via hole 100*a*.

Of course, the light irradiated from the light source unit 1 to the wafer 100 is irradiated to the surface opposite to the surface of the wafer 100 in which the via hole 100*a* has been formed, and the light is reflected by three reflecting surfaces of the wafer 100.

Figure 3:
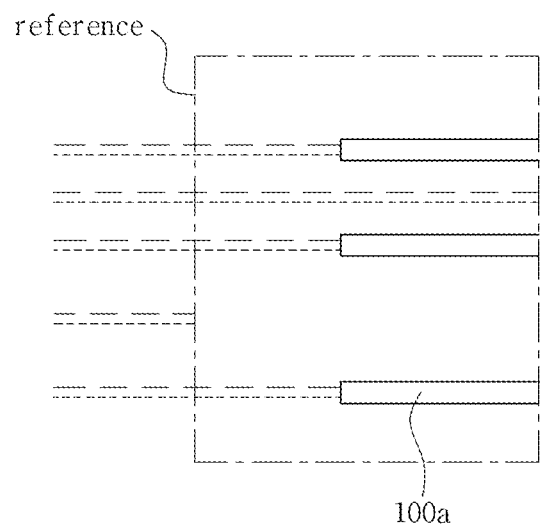
FIG. 3 is a schematic diagram illustrating a light reflection path when a depth and a diameter of a via hole are measured using the device for measuring a via hole of a silicon wafer in FIG. 2.

That is, since the light is reflected by the interfaces of the rear surface (when the surface having the via hole formed therein is assumed to be a front surface), the front surface, and the bottom surface of the via hole 100*a* of the wafer 100 as illustrated in FIG. 3, the depth of the via hole 100*a* can be measured by measuring an interference signal between the three measurement lights (reflected light) and the reference light reflected by the reference mirror.

When the reference mirror is not used like this, the rear surface may be set as a reference surface and a light reflected by the rear surface may be set as the reference light as illustrated in FIG. 2, or the front surface may be set as the reference surface and a light reflected by the front surface may be set as the reference light, although not shown.

Figure 4:
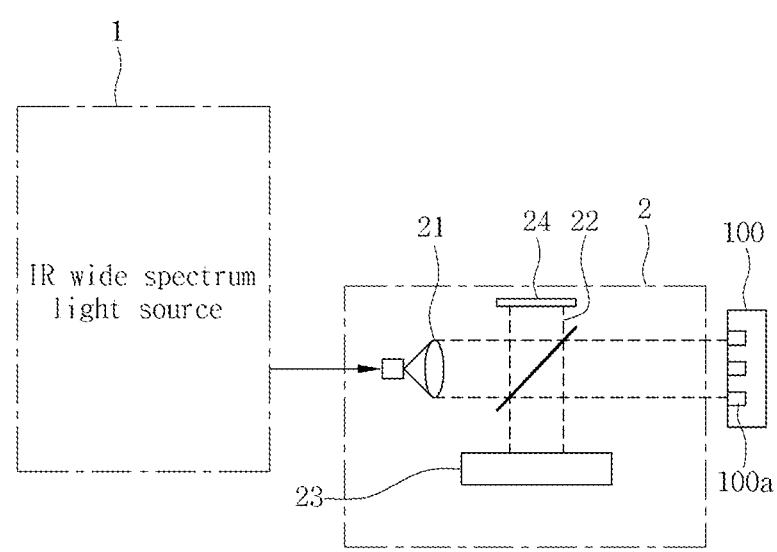
FIG. 4 is a diagram illustrating a configuration of a device for measuring a via hole of a silicon wafer according to another embodiment of the present invention.

Of course, when the reference mirror 24 is provided as illustrated in FIG. 4, the light reflected by the reference mirror is set as the reference light.

Another embodiment of the present invention will be described in detail with reference to FIG. 5.

In this embodiment, a principle of measuring the depth and the diameter of the via hole using an interference phenomenon is the same as the those of the other embodiments, and a configuration is the same as those of the other embodiments except for the following difference.

Figure 5:
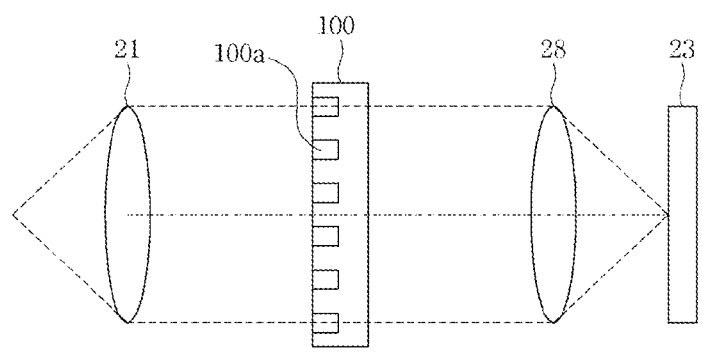
FIG. 5 is a diagram illustrating a configuration of an interferometer of a device for measuring a via hole of a silicon wafer according to another embodiment of the present invention.

As illustrated in FIG. 5, a broadband infrared light generated by a light source is irradiated to a front surface of a silicon wafer and is first transmitted through a bottom surface of the via hole. A part of the light is transmitted through a rear surface, the other part is reflected by the rear surface, and a part of the reflected light is reflected by a bottom surface of the via hole again. Accordingly, the infrared light transmitted without being reflected and the infrared light reflected twice after being transmitted through the via hole generate an interference signal according to an optical path difference. A distance between the via hole and the rear surface can be measured by measuring the interference signal using the detector.

In the case of an interferometer having the same structure as that illustrated in FIG. 5, a condenser lens 28 may be provided between the silicon wafer and the detector. In this case, the reference light is a light transmitted through the silicon wafer surface in which a via hole has not been formed, and a travelling speed of the light transmitted through the via hole is changed due to a refractive index difference. Accordingly, an optical path difference is generated and the two lights are condensed by the condenser lens 28 to obtain an interference signal.

Figure 6:
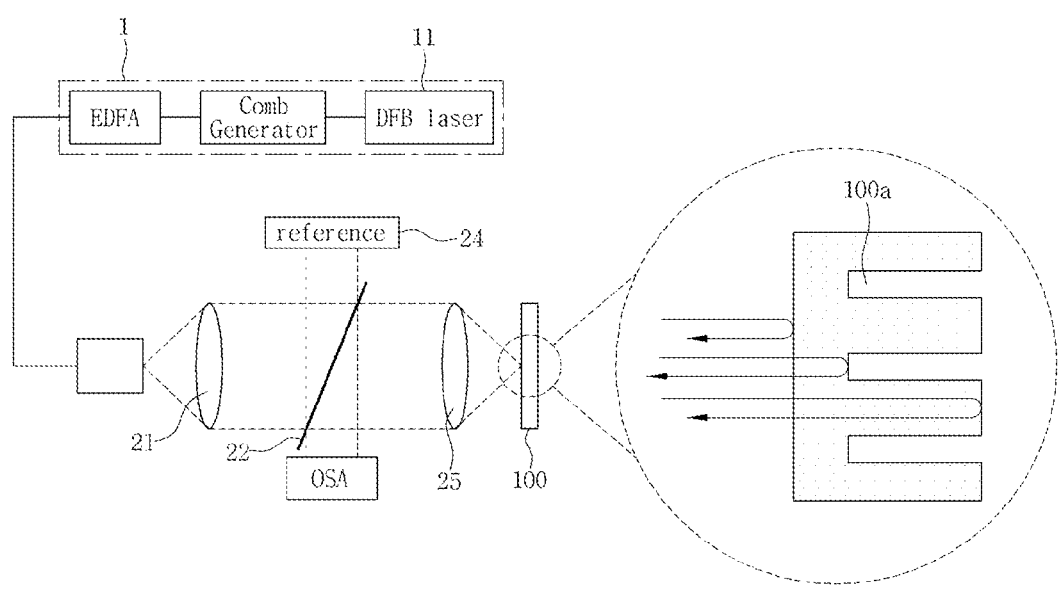
FIG. 6 is a diagram illustrating a configuration of a device for measuring a via hole of a silicon wafer according to a preferred embodiment of the present invention.
Figure 7:
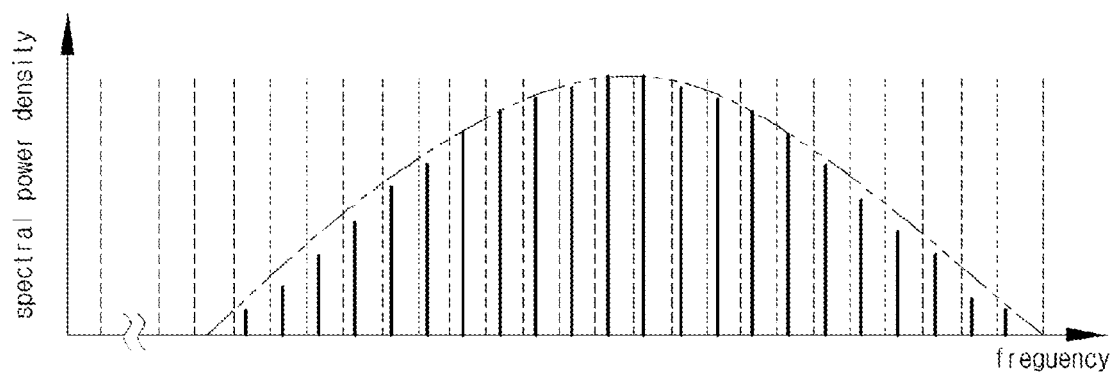
FIG. 7 is a diagram illustrating a mode locked pulse laser light represented in a frequency domain.

Hereinafter, a device for measuring a via hole of a silicon wafer according to a preferred embodiment of the present invention will be described with reference to FIGS. 6 and 7, and a description of the same configuration as those of the other embodiments will be omitted.

A light source unit that generates a broadband infrared light includes a seed laser, an optical modulator, and an optical amplifier. The seed laser is a DFB laser 11 that generates a laser light having a single wavelength whose center wavelength is 1541 nm. The laser light having a single wavelength emitted from the DFB laser is incident on a phase modulation optical comb generator to generate a spectrum whose repetition rate ranges from 20 to 30 GHz and bandwidth ranges from 15 nm to 25 nm. Preferably, the repetition rate is 10 MHz or more, and the bandwidth is 10 nm or more. FIG. 7 illustrates an optical comb represented in a frequency domain. This optical comb is represented by frequency components well defined at certain intervals around a center frequency in the frequency domain. In a time domain, a laser pulse including several frequency components is repeated in a certain period, which is generally called a pulse laser. Thus, the pulse laser forming the optical comb has several frequency components, but the respective frequency components are very well defined and stabilized. Accordingly, it is advantageous in period analysis for the interference signal, thus further improving precision of measurement of the depth of the via hole.

The optical comb generator is a kind of frequency generator. A repetition rate of the broadband laser pulse generated by the optical comb generator is locked to a reference clock (Rb-reference clock) and stabilized. The generated optical comb is amplified by the amplifier 13 to have a light amount sufficient to be actually applied to and used in the interferometer. As the amplifier, an Er doped fiber amplifier (EDFA) may be used.

The amplified light is input to an interferometer 2, and the light collimated through the collimation lens 21 is split by a beam splitter 22 and incident on a wafer 100 through a condenser lens 25. A light reflected by an interface of any one of the surfaces among lights reflected and returned from silicon wafer 100 or a light reflected by a reference mirror is used as a reference light. An interference signal with a measurement light is detected by the detector 23 and calculated to measure the depth and diameter or the width of the via hole 100a.

Meanwhile, it is desirable for the pulse laser generating the spectrum in the optical comb generator to be a femto-second laser, i.e., for a pulse width in a time domain to be a few to hundreds of femto seconds. In this case, interference is generated only for a very short period of time, thereby improving measurement resolution, and a peak light amount of an oscillated pulse is very large, thereby improving a signal to noise ratio.

Since the femto-second laser oscillator itself generates a pulse laser forming the optical comb, it is unnecessary to form the optical comb from a separate seed laser.

With the device and method of measuring a via hole according to the preferred embodiments of the present invention described above, it is possible to accurately confirm whether the via hole is defective rapidly in a non-destructive manner. Accordingly, utilization in a 3D semiconductor packing process is excellent, the yield of a semiconductor package is improved, and influence of mechanical vibration on measurement quality is minimized.

INDUSTRIAL APPLICABILITY

With the device and method of measuring via hole according to the present invention as described above, it is possible to accurately confirm whether the via hole is defective rapidly in a non-destructive manner. Accordingly, when the device or the method are applied to a 3D semiconductor packing process, it is possible to confirm whether the via hole of the silicon wafer is defective. Thus, utilization is excellent and the yield of a semiconductor package is improved. Further, since influence of mechanical vibration on measurement quality is minimized, it is possible to rapidly and accurately to measure the depth and the diameter of the via hole.

The device may also be used as a device that measures the via hole as well as several fine structures of the silicon wafer.

What is claimed is:

1. A device for measuring a via hole of a silicon wafer, the device comprising a light source unit, and an interferometer that irradiates a light generated from the light source unit to the silicon wafer and measures a depth of the via hole formed in the wafer from an interference signal of a light reflected by the silicon wafer, wherein the light source unit generates a broadband infrared light, the interferometer senses an interference signal that is generated as the broadband infrared light is reflected by interfaces of a bottom surface of the via hole and a front surface or a rear surface of the silicon wafer, and optical path differences for a plurality of frequency components are simultaneously acquired through spectrum period analysis for the interference signal to measure a depth and a diameter of the via hole, and wherein the interferometer includes:

a collimation lens that converts the broadband infrared light output from the light source unit to a parallel light;

a condenser lens that is arranged to face the collimation lens with the silicon wafer interposed therebetween, and condenses the infrared light transmitted through the silicon wafer after passing through the collimation lens;

a detector that is arranged to face the condenser lens and detects an interference signal caused by an optical path difference between an infrared light passing through the via hole formed in the silicon wafer and an infrared light transmitted through a portion of the silicon wafer in which a via hole has not been formed.

2. A via hole measurement method using a device for measuring a via hole of a silicon wafer according to claim 1, wherein:

the broadband infrared light from the light source unit is irradiated to the front surface or the rear surface of the silicon wafer and reflected by interfaces of both surfaces of the silicon wafer and the bottom surface of the via hole, a light reflected by one of the surfaces of the wafer is used as the reference light, and an interference signal of the reference light and the infrared light reflected by the bottom surface of the via hole is measured to measure the depth of the via hole.

3. The method according to claim 2, wherein:

the interference signal of the lights reflected by the interfaces of both surfaces of the silicon wafer and the interface of the bottom surface of the via hole and the reference light is measured to measure the diameter of the via hole while finely moving the wafer in a direction perpendicular to the broadband infrared light irradiated from the light source unit.

4. The device according to claim 1, wherein the interferometer includes a spectrum analyzer and acquires an interference signal according to each frequency component.

5. The device according to claim 1, wherein the interferometer is provided to face a surface opposite to the surface of the silicon wafer in which the via hole has been formed, and senses a light obtained as a broadband infrared irradiated from the light source is transmitted through the silicon wafer and reflected by an interface of the bottom surface of the via hole or the opposite surface of the wafer.

6. The device according to claim 1, wherein the light source unit includes:

a seed laser that generates a single wavelength laser light in an infrared region;

a frequency generator that generates a broadband infrared light from the infrared laser light output by the seed laser; and an amplifier that amplifies the broadband infrared light generated by the frequency generator to have a light amount sufficient to be applied to the interferometer.

7. The device according to claim 1, wherein the broadband infrared light generated by the light source unit has a frequency interval ranging from 1 kHz to 100 GHz and a bandwidth ranging from 0.1 nm to 2000 nm.

8. The device according to claim 1, wherein the broadband infrared light generated by the light source unit includes a pulse laser.

9. The device according to claim 1, wherein the interferometer further includes a beam splitter that transmits a light passing through the collimation lens and reflects the light reflected by the wafer to split a path of the light, and wherein the detector uses a light reflected by one of the surfaces of the wafer among the lights reflected by the wafer as a reference light and detects an interference signal that is a combination of a measurement light and the reference light.

10. The device according to claim 9, wherein the interferometer further includes a reference mirror that provides the reference light to the detector using the light reflected by the beam splitter.

\* \* \* \* \*